United States Patent
Williams et al.

(10) Patent No.: US 9,664,560 B2
(45) Date of Patent: May 30, 2017

(54) DOUBLE-GRATING SURFACE-ENHANCED RAMAN SPECTROSCOPY

(75) Inventors: R. Stanley Williams, Portola Valley, CA (US); Zhiyong Li, Foster City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 261 days.

(21) Appl. No.: 14/381,009

(22) PCT Filed: Mar. 6, 2012

(86) PCT No.: PCT/US2012/027871
§ 371 (c)(1),
(2), (4) Date: Aug. 26, 2014

(87) PCT Pub. No.: WO2013/133804
PCT Pub. Date: Sep. 12, 2013

(65) Prior Publication Data
US 2014/0375990 A1    Dec. 25, 2014

(51) Int. Cl.
*G01J 3/02*    (2006.01)
*G01J 3/44*    (2006.01)
*G01N 21/65*    (2006.01)

(52) U.S. Cl.
CPC ............. *G01J 3/0205* (2013.01); *G01J 3/44* (2013.01); *G01N 21/658* (2013.01);
(Continued)

(58) Field of Classification Search
CPC ......... G01N 21/658; G01N 21/65; G01J 3/44; G01J 3/4412
See application file for complete search history.

(56) References Cited

U.S. PATENT DOCUMENTS 6,583,873 B1 * 6/2003 Goncharov ............... G01J 3/06
356/326
8,842,265 B2 * 9/2014 Fattal ............... B29D 11/00346
356/301
(Continued)

FOREIGN PATENT DOCUMENTS

| CN | 102097497 | 6/2011 |
|---|---|---|
| CN | 102201483 | 9/2011 |
| JP | 2008034482 | 2/2008 |

OTHER PUBLICATIONS

Andre Christ, "Optical properties of metallic photonic crystal structures," Aug. 2005, Disertation, Max-Planck-Institut fur Festkorperforschung Stuttgart.*
(Continued)

*Primary Examiner* — Kara E Geisel
*Assistant Examiner* — Violeta A Prieto
(74) *Attorney, Agent, or Firm* — HP Inc. Patent Department

(57) ABSTRACT

A double-grating surface-enhanced Raman spectrometer. The spectrometer includes a substrate; a plurality of nanofingers carried by the substrate, the nanofingers arranged to define a first optical grating; a light source oriented to project a beam of light toward the first optical grating; a second optical grating oriented to receive a beam of light scattered from the first optical grating; and a detector oriented to receive a beam of light scattered from the second optical grating.

19 Claims, 9 Drawing Sheets

(52) U.S. Cl.
CPC ...... *G01J 3/4412* (2013.01); *G01N 2201/068* (2013.01); *G01N 2201/06113* (2013.01)

(56) References Cited

U.S. PATENT DOCUMENTS

| | | | |
|---|---|---|---|
| 2005/0084912 A1 | 4/2005 | Poponin | |
| 2008/0309931 A1* | 12/2008 | Silberberg | G01J 3/44 356/301 |
| 2010/0067000 A1 | 3/2010 | Baumberg et al. | |
| 2010/0091274 A1 | 4/2010 | Bratkovski et al. | |
| 2010/0284001 A1* | 11/2010 | Moskovits | G01N 21/658 356/301 |
| 2011/0134422 A1* | 6/2011 | Umapathy | G01J 3/10 356/301 |
| 2012/0033213 A1* | 2/2012 | Yang | G01J 3/02 356/326 |
| 2012/0081703 A1* | 4/2012 | Moskovits | G01N 21/658 356/301 |
| 2012/0268736 A1* | 10/2012 | Fattal | B29D 11/00346 356/301 |

OTHER PUBLICATIONS

Deng et al., Single-order, Subwavelength Resonant Nanograting as a Uniformly Hot Substrate for Surface-enhanced Raman Spectroscopy; http://www.mendeley.com/research/singleorder-subwavelength-resonant-nanograting-uniformly-hot-substrate-surfaceenhanced-raman-spectroscopy/>; vol. 10. On pp. 1780-1786 ; 2010.

Schider et al.; Optical Properties of Ag and Au Nanowire Gratings; http://jap.aip.org/resource/1/japiau/v90/i8/p3825_s1?isAuthorized=no >; vol. 90; Jul. 25, 2001.

* cited by examiner

DOUBLE-GRATING SURFACE-ENHANCED RAMAN SPECTROSCOPY

BACKGROUND

Spectroscopy refers to determining the nature of a substance by measuring a parameter of energy emitted by the substance. For example, if a laser beam is scattered off of a substance, most of the photons will be elastically scattered (that is, their wavelength will remain the same) but some will be inelastically scattered (their wavelength be changed as a result of an exchange of energy between the incident photons and the molecules of the substance. This change of wavelength is called the Raman Effect. The substance can be identified by measuring how much the wavelength has shifted. The Raman Effect can be enhanced by adsorbing molecules of the substance onto a rough metal surface and then exposing them to the incident laser beam. This technique is referred to as surface-enhanced Raman spectroscopy (SERS). The enhancement factor is so high—as much as $10^{11}$—that individual molecules of the substance can be identified. A suitable surface may be prepared by forming tiny projections called nanofingers on a silicon substrate; in some instances, tips of the nanofingers are thinly coated with a metal such as gold or silver. When an unknown substance is adsorbed onto the surface, capillary action causes the nanofingers to bend toward each other, trapping individual molecules. The nanofingers may be thought of as tiny tweezers that hold these individual molecules of the unknown substance up to the laser beam for analysis. When the laser beam is scattered off of the nanofingers, it is directed through a precision optical path that includes various optical components including a filter to attenuate any elastically-scattered photons and then to a photodetector such as a charge-coupled device (CCD). The photodetector provides a signal that is analyzed to determine the wavelength shift and thereby identify the substance.

BRIEF DESCRIPTION OF THE DRAWINGS

The figures are not drawn to scale. They illustrate the disclosure by examples.

DETAILED DESCRIPTION

Figure 1:
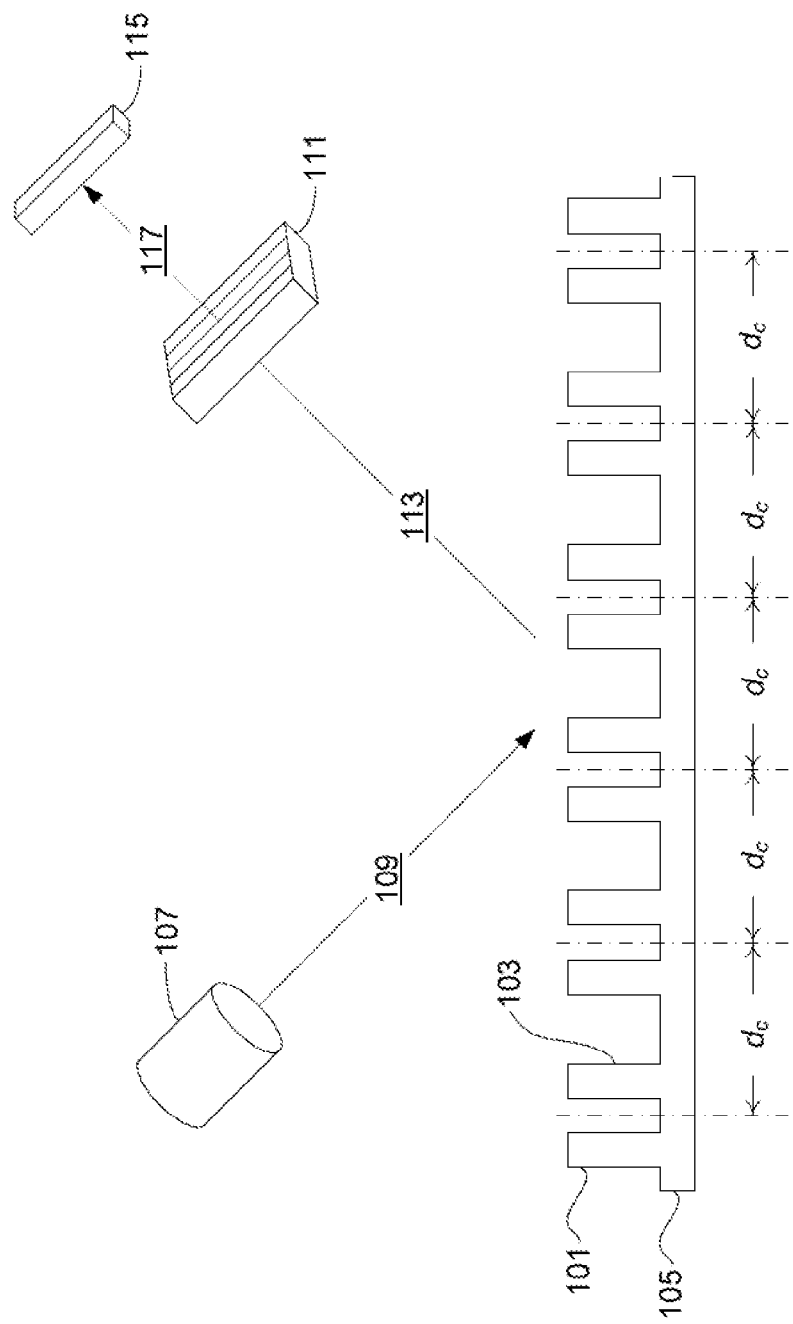
FIG. 1 is a diagram of a double-grating surface-enhanced Raman spectrometer according to an example.

Illustrative examples and details are used in the drawings and in this description, but other configurations may exist and may suggest themselves. Parameters such as voltages, temperatures, dimensions, and component values are approximate. Terms of orientation such as up, down, top, and bottom are used only for convenience to indicate spatial relationships of components with respect to each other, and except as otherwise indicated, orientation with respect to external axes is not critical. For clarity, some known methods and structures have not been described in detail. Methods defined by the claims may comprise steps in addition to those listed, and except as indicated in the claims themselves the steps may be performed in another order than that given. Accordingly, the only limitations are imposed by the claims, not by the drawings or this description.

The systems and methods described herein may be implemented in various forms of hardware, software, firmware, special purpose processors, or a combination thereof. At least a portion thereof may be implemented as an application comprising program instructions that are tangibly embodied on one or more program storage devices such as hard disks, magnetic floppy disks, RAM, ROM, and CDROM, and executable by any device or machine comprising suitable architecture. Some or all of the instructions may be remotely stored and accessed through a communication facility; in one example, execution of remotely-accessed instructions may be referred to as cloud computing. Some of the constituent system components and process steps may be implemented in software, and therefore the connections between system modules or the logic flow of method steps may differ depending on the manner in which they are programmed.

There is a growing need in many areas of study for spectrometers that can deliver optimal Raman-enhanced spectra. Just one example is the need for spectrometers to identify minute quantities of DNA in biotech applications. Particularly needed now is an economical, compact spectrometer to meet the increasing demand for Raman-enhanced spectral analyses while avoiding the high cost and physical bulk of existing instruments.

FIG. 1 depicts an example of a double-grating surface-enhanced Raman spectrometer. A plurality of nanofingers such as the nanofingers 101 and 103 are carried by a substrate 105. The nanofingers are arranged to define a first optical grating, to be described in more detail presently. A light source 107 such as a laser is oriented to project a beam of light 109 toward the first optical grating. A second optical grating 111 is oriented to receive a beam of light 113 scattered from the first optical grating. A detector 115 is oriented to receive a beam of light 117 scattered from the second optical grating.

Figure 2:
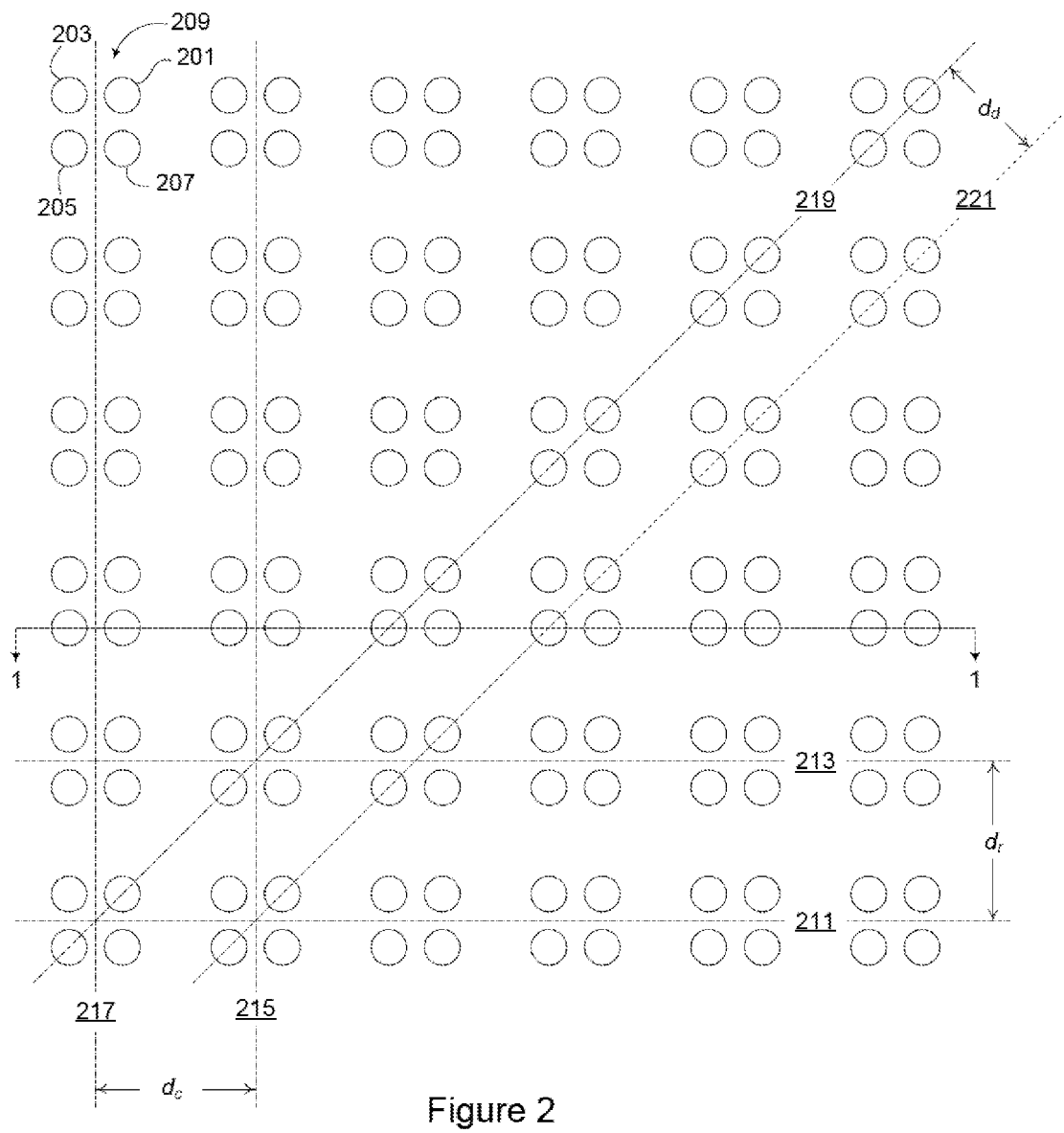
FIG. 2 is a top view of nanofingers arranged in groups of four to define an optical grating according to an example.

As shown in FIG. 2, in some examples the nanofingers are arranged in groups of four. For example, nanofingers 201, 203, 205, and 207 are disposed to define a square group 209. In one orientation of the nanofingers with respect to the incident light beam 109, the optical grating is defined by rows of the nanofinger groups, such as a row 211 of four-nanofinger groups and an adjacent row 213 of four-nanofinger groups. The rows are separated by a distance $d_r$. In another orientation, the optical grating is defined by columns of the nanofinger groups, for instance a column 215 and an adjacent column 217 separated by a distance $d_c$. In the example of FIG. 2 the distances $d_r$ and $d_c$ are equal, but in general this need not be the case.

In an example of another orientation of the nanofingers with respect to the incident light beam 209, the optical grating is defined by diagonals along the groups such as a diagonal 219 and an adjacent diagonal 221. The diagonals 219 and 221 are separated by a distance $d_d$. In the example shown, $d_r = d_c = d_d\sqrt{2}$.

FIG. 1 presents a side view of the nanofingers in combination with the other components of the spectrometer, whereas FIG. 2 presents a top view of the nanofingers without any other spectrometer components. The side view of the nanofingers in FIG. 1 may be considered as a sectional view along the line 1-1 in FIG. 2. The nanofingers are shown as cylindrical, but this is not critical and the nanofingers may be fabricated in different shapes as desired.

Figure 3:
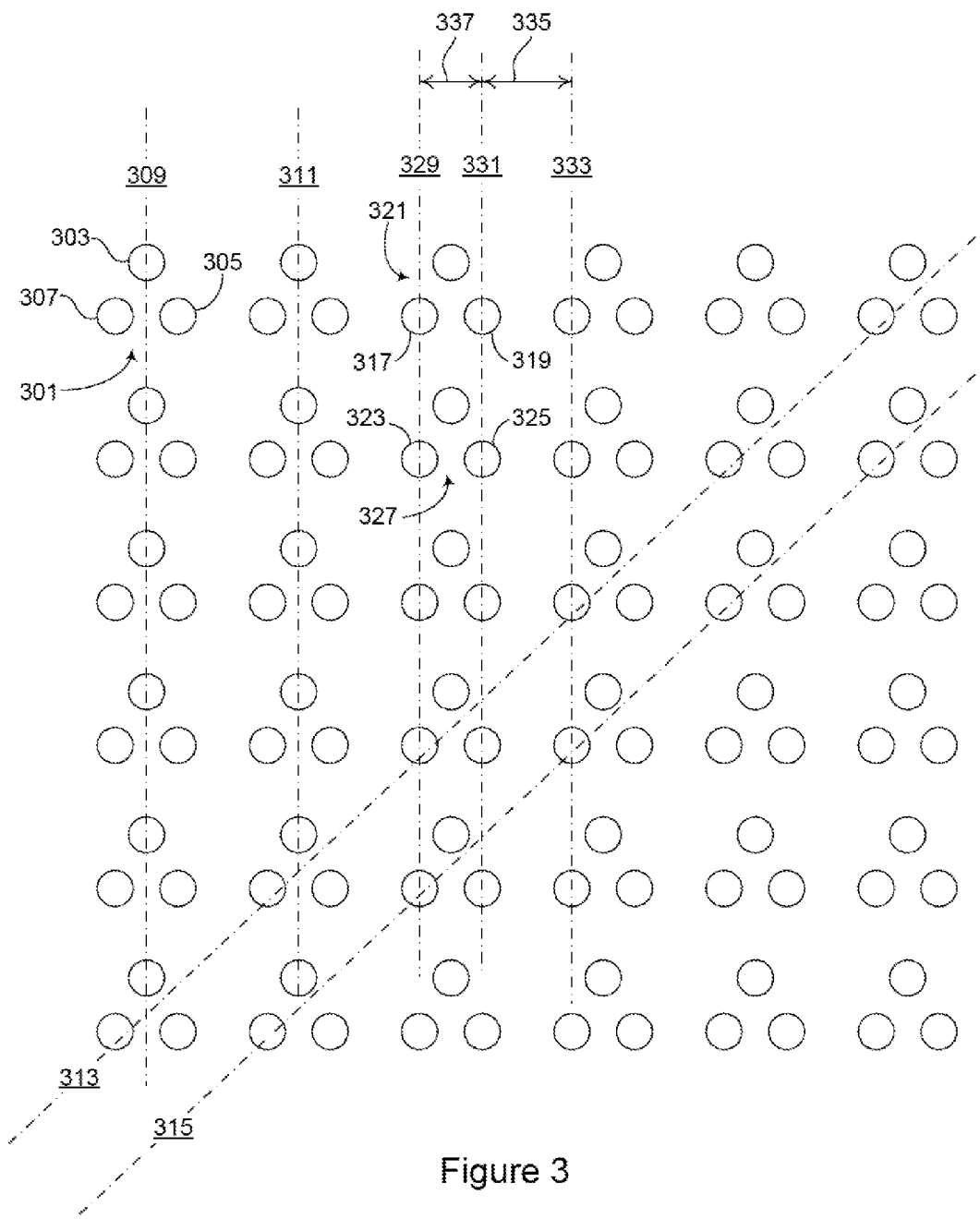
FIG. 3 is a top view of nanofingers arranged in groups of three to define an optical grating according to an example.

FIG. 3 illustrates an example in which the nanofingers are arranged in groups of three, such as a group 301 formed by nanofingers 303, 305, and 307, to define the optical grating. In the illustration each group of three nanofingers is laid out to form a group shape of an equilateral triangle, but this is not critical and each group of three nanofingers may be laid out to form another group shape as desired. The nanofingers may be oriented with respect to the incident light beam 109 so that columns of the groups such as a column 309 and an adjacent column 311 define the grating. In another example the nanofingers are oriented with respect to the incident light beam such that the optical grating is defined by diagonals along the groups such as a diagonal 313 and an adjacent diagonal 315. In another example the optical grating is defined by rows (not depicted in the drawing) of 3-nanofinger groups.

In other examples the optical grating is defined by successive columns or rows of adjacent nanofingers rather than by 3-nanofinger groups. In one such example, a nanofinger 317 is adjacent a nanofinger 319 in a group 321, and a nanofinger 323 is adjacent a nanofinger 325 in a group 327 that is adjacent the group 321. A column 329 is defined by the nanofingers 317, 323, and other similarly-situated nanofingers. A column 331 adjacent the column 329 is defined by the nanofingers 319, 325, and other similarly-situated nanofingers. Another column 333, adjacent the column 331, is defined by nanofingers in adjacent groups. The groups may be disposed such that a distance 335 between the columns 331 and 333 is the same as, or different from, a distance 337 between the columns 329 and 331, as desired.

Figure 4:
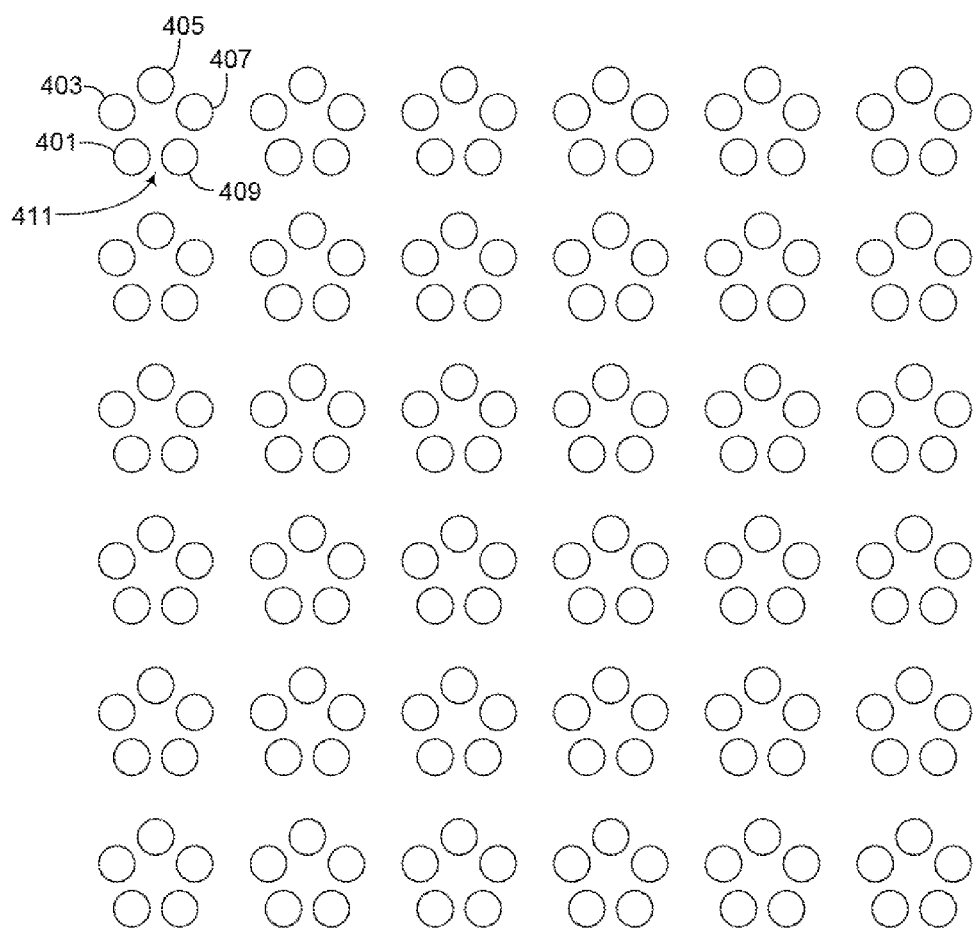
FIG. 4 is a top view of nanofingers arranged in groups of five to define an optical grating according to an example.

FIG. 4 illustrates an example in which nanofingers are arranged in groups of five, and these five-nanofinger groups define the first optical grating. A group of five nanofingers 401, 403, 405, 407, and 409 are arranged to form a group 411. In this example the five-nanofinger group is in the shape of an equilateral pentagon but in other examples the group of five may be shaped differently as desired. The nanofingers may be oriented with respect to the light source such that rows, columns, or diagonals of the groups or of nanofingers in the groups define the first optical grating.

Figure 5:
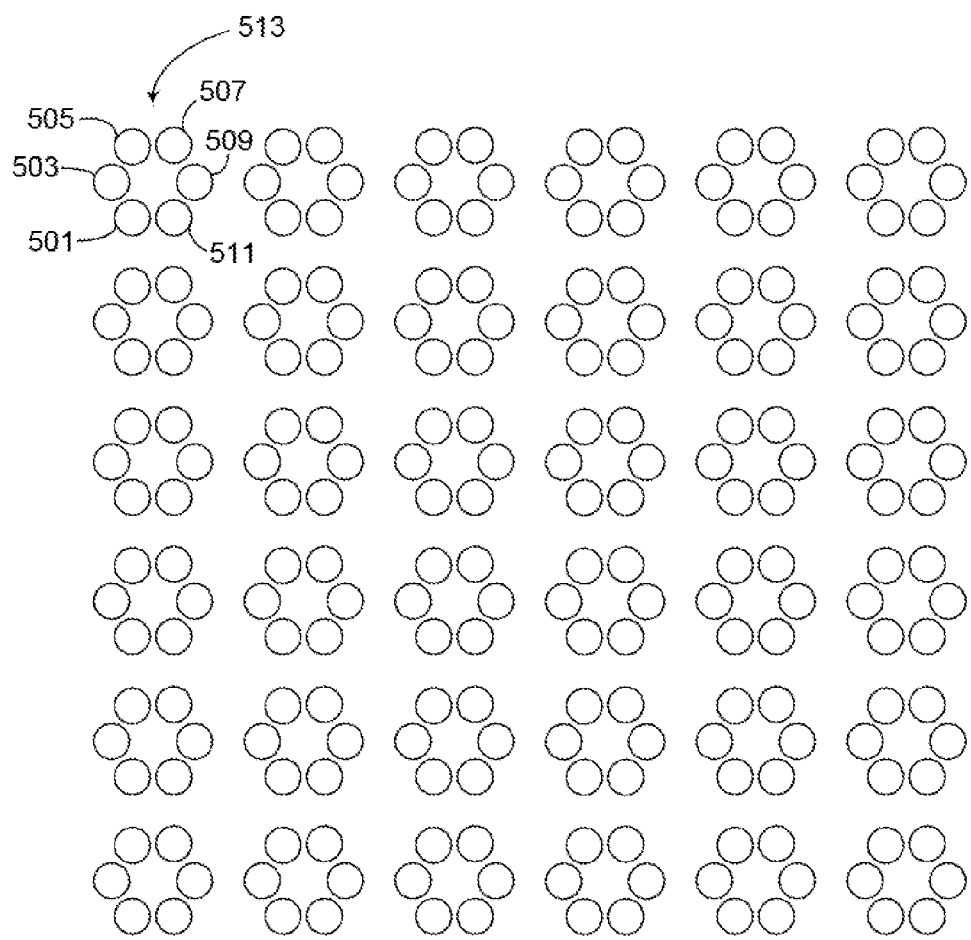
FIG. 5 is a top view of nanofingers arranged in groups of six to define an optical grating according to an example.

FIG. 5 illustrates an example in which nanofingers are arranged in groups of six to define the first optical grating. A group of six nanofingers 501, 503, 505, 507, 509 and 511 are arranged in this instance to form a group 513 in the shape of an equilateral hexagon. As with the preceding examples, the six nanofingers in the group need not be laid out to form an equilateral hexagon. The 6-nanofinger groups may be oriented with respect to the light source such that rows, columns, or diagonals define the first optical grating.

Figure 6:
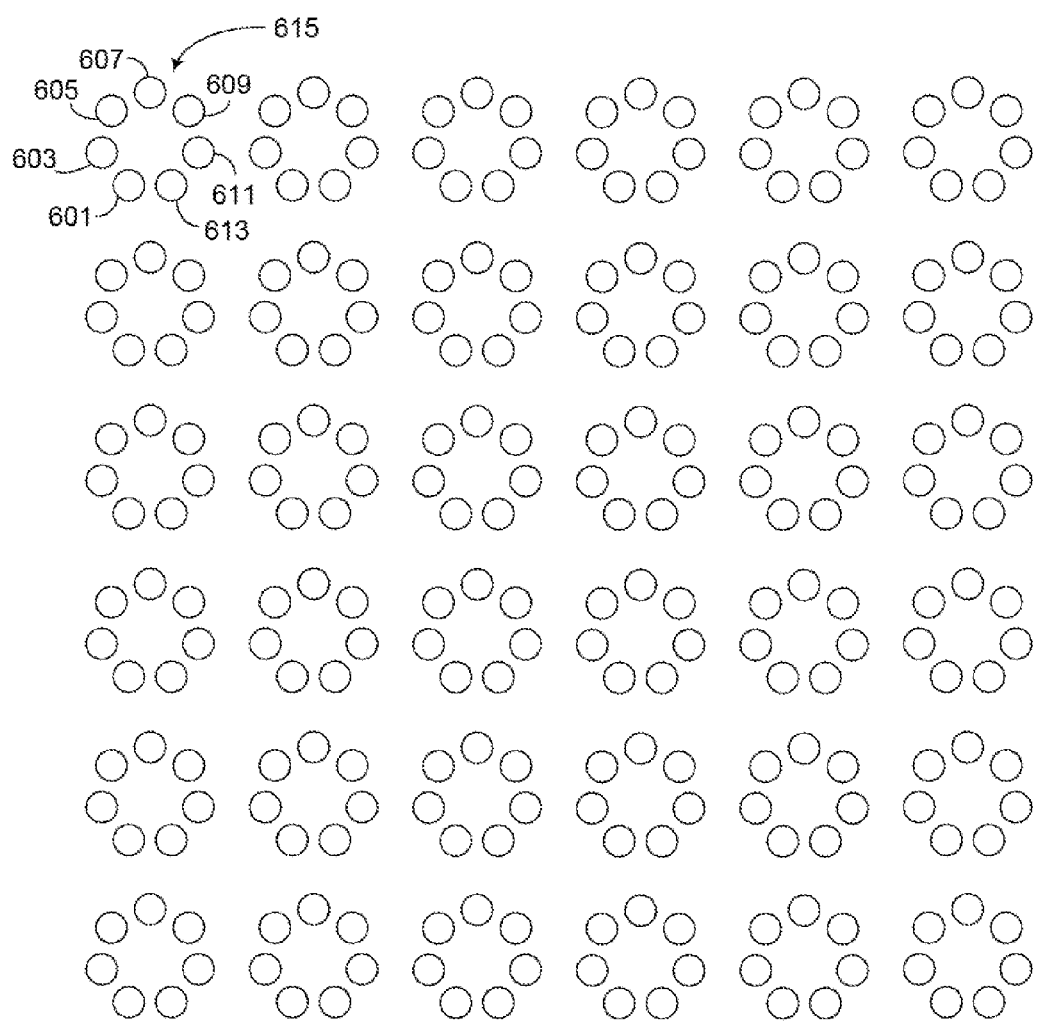
FIG. 6 is a top view of nanofingers arranged in groups of seven to define an optical grating according to an example.

FIG. 6 illustrates an example in which nanofingers are arranged in groups of seven to define the first optical grating. Seven nanofingers 601, 603, 605, 607, 609, 611, and 613 are arranged in a group 615 which in this case is in the shape of an equilateral heptagon. As with the preceding examples, the seven nanofingers need not be laid out in this shape, and the groups may be oriented with respect to the light source such that rows, columns, or diagonals define the first optical grating.

The nanofingers may be arranged otherwise than in the foregoing examples to define the first optical grating. Other numbers of groups may be used, and the number of groups in a row need not be the same as the number of groups in a column.

Figure 7:
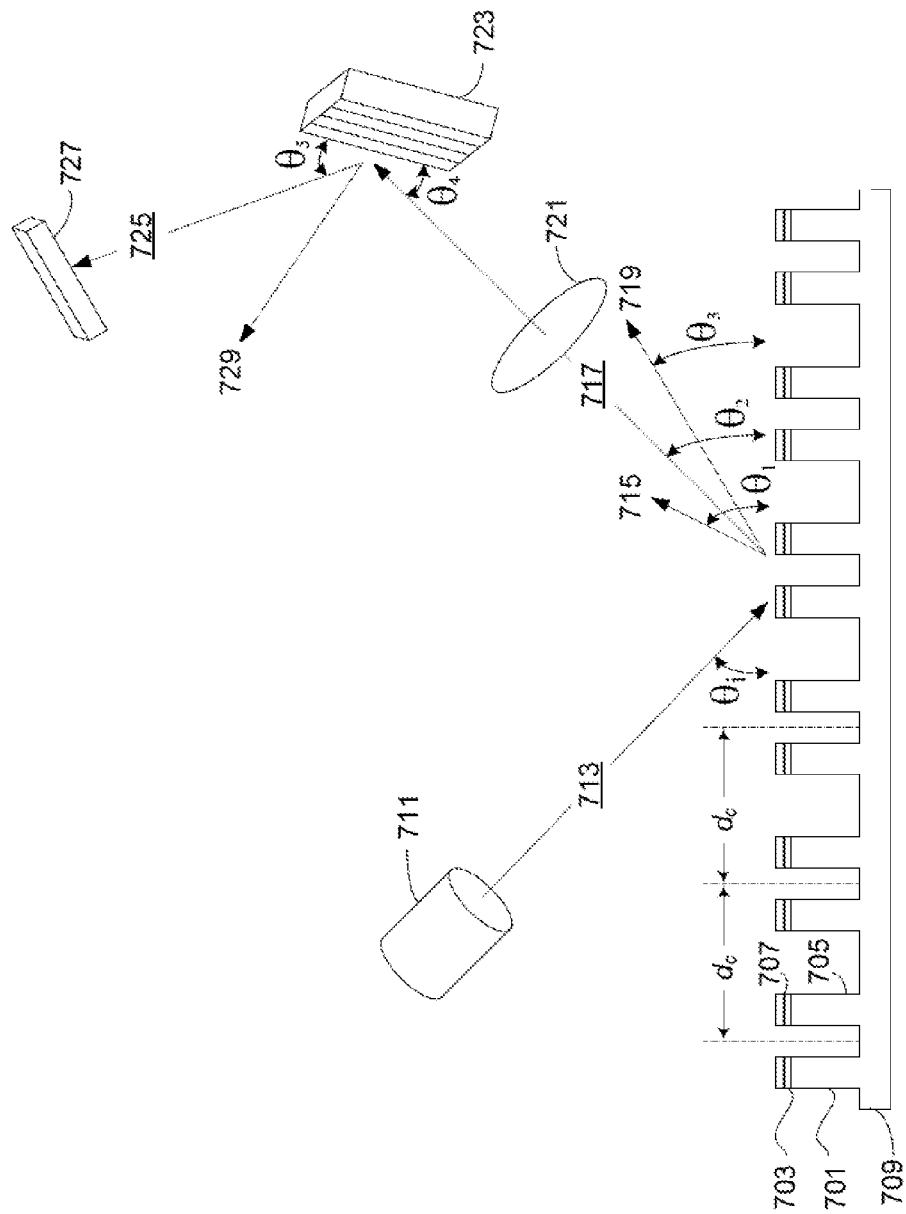
FIG. 7 is a diagram of another double-grating surface-enhanced Raman spectrometer according to an example.

As noted above, in some examples tips of the nanofingers are coated with a metal such as gold or silver. This is shown in FIG. 7 in which a tip of a nanofinger 701 has been coated with metal 703, a tip of a nanofinger 705 has been coated with metal 707, and so on. The nanofingers are carried by a substrate 709. The nanofingers may be formed by nanoimprinting, optical lithography, embossing, or etching the substrate, or by growing or depositing them on the substrate, or some other method as may be convenient.

In the example of FIG. 7, a light source 711 projects a beam of light 713 toward the nanofingers. As in previous examples, the nanofingers are laid out to define a first optical grating. In this example the nanofingers are laid out in groups of four, oriented so that columns of groups separated by a distance $d_c$ define the first optical grating. As discussed above, the nanofingers may be laid out in other ways to define the groups.

The light beam 713 is incident on the first optical grating at an angle $\theta_i$. When the incident light is reflected from the first optical grating, the wavelength of some of the incident light is shifted (the Raman Effect) by molecules of the unknown substance (not shown in FIG. 7) that have been trapped between the nanofingers. Depending on the nature of the unknown substance, there will be n different wavelengths in the reflected light. Each of these wavelengths $\lambda_x$, where x=1, 2, . . . , n, is reflected at an angle of reflection $\theta_x$ that is determined according to the equation:

$$d_c (\sin \theta_i + \sin \theta_x) = \lambda_x$$

where $d_c$ is the distance between grating features, $\theta_i$ is the angle of incidence of the light beam, $\lambda_x$ is the wavelength of the reflected light, and $\theta_x$ is the angle of reflection of light having wavelength $\lambda_x$.

For any given wavelength, there can be more than one reflected light beam. Each such reflected light beam is reflected at an angle that is determined by an integer multiple m of the wavelength. For the present discussion, it will be assumed that m=1. Also, in this example it will be assumed that the incident light beam is scattered by the first optical grating into three light beams 715, 717, and 719 of wavelength $\lambda_1$, $\lambda_2$, and $\lambda_3$ respectively, at angles of reflection $\theta_1$, $\theta_2$, and $\theta_3$ respectively.

After being reflected by the first optical grating defined by the nanofingers, the light passes through a lens 721 and onto a second optical grating 723.

In the example of FIG. 7 it is assumed that the wavelength of interest at the moment is $\lambda_2$. Accordingly, the nanofingers have been disposed relative to the incident light source 711 and the lens 721 such that only reflected light of that wavelength passes through the lens 721 to the second optical grating 723. Light 715 and 719 of other wavelengths reflects at angles $\theta_1$ and $\theta_3$ and does not enter the lens.

The light beam 717 is incident on the second optical grating 723 at an angle of incidence $\theta_4$ and is reflected at an angle of reflection $\theta_5$ to form a reflected light beam 725 that continues to a detector 727. As with the first optical grating, so with the second one the angle of reflection is determined both by the angle of incidence and by the wavelength of the incident light. The second optical grating is oriented with respect to the path of the incident light beam 717 and the detector 727 such that only light having the desired wavelength is reflected to the detector and light of other wavelengths, such as a light beam 729, does not pass to the detector. In some examples the second optical grating is oriented to receive light over a range of wavelengths from the first optical grating. In this way the two optical gratings determine a desired range of wavelengths such that any light not having a wavelength within the desired range is attenuated or does not reach the detector at all. In some examples the two optical gratings are specially paired with each other for optimal performance over a desired range of wavelengths.

More than one optical lens may be used, and the optical path may be more complex and have more optical components, than depicted in FIG. 7. In other examples, the lens may be omitted.

Figure 8:
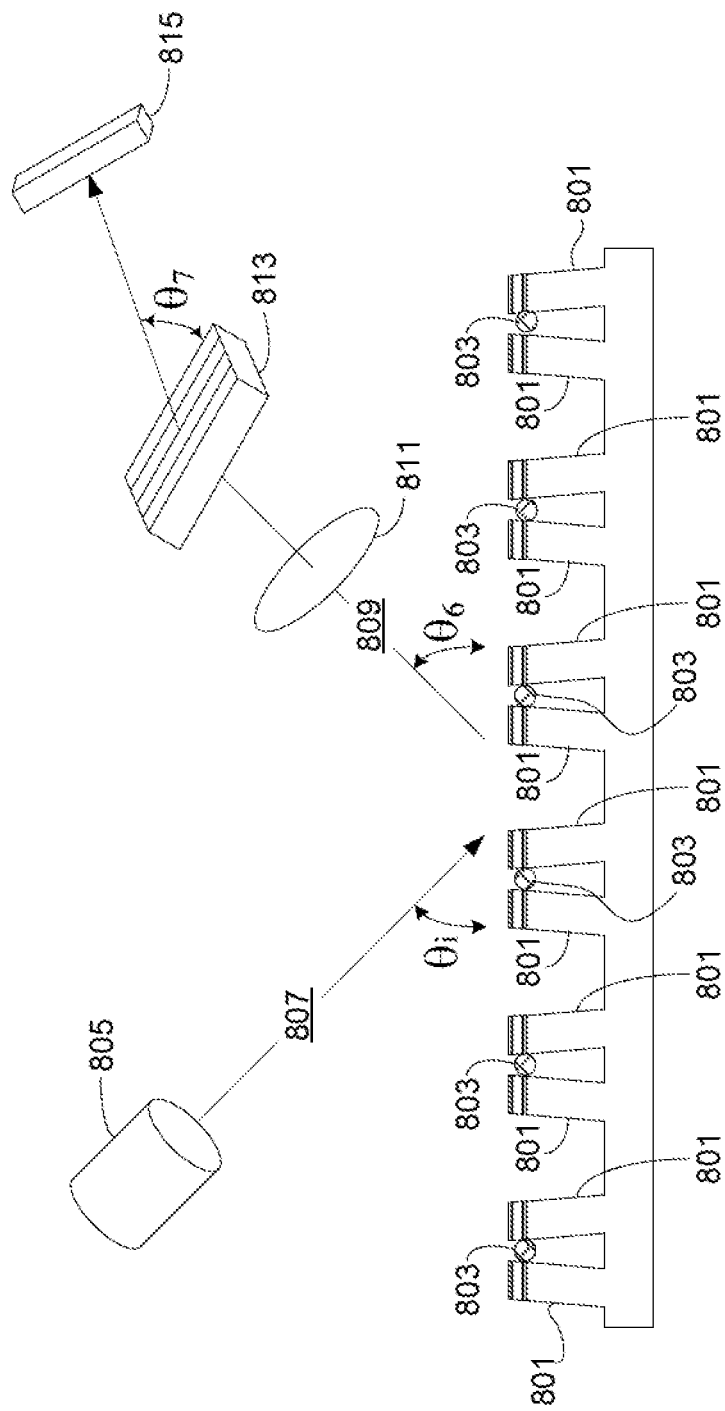
FIG. 8 is a diagram of another double-grating surface-enhanced Raman spectrometer according to an example.

Another example of a double-grating surface-enhanced Raman spectrometer is shown in FIG. 8. In this example, nanofingers 801 are shown slightly deformed under capillary action, trapping molecules 803 of an unknown substance. A light source 805 provides a beam of light 807 that strikes the first optical grating defined by the nanofingers at an angle of incidence $\theta_1$ and is reflected. As in the previous example, the angle of reflection is determined by the wavelength, and in the usual case there will be more than one reflected beam each of different wavelength and each at a different angle of reflection. To avoid cluttering the drawing, only the reflected light beam $09 having a desired wavelength is shown. The light beam 809 is directed to an optical lens 811. The angle of reflection of this light beam is $\theta_6$ and the first optical grating defined by the nanofingers is oriented with respect to the light source 805 and the lens 811 in such manner than only light having the desired wavelength is reflected from the first optical grating to the lens 811. From the lens the reflected light travels to a second optical grating 813, in this case a transmissive grating rather than the reflecting grating shown in FIG. 7.

The light beam 809 is refracted by the optical grating 813 at an angle $\theta_7$ that, as before, is determined by the angle of incidence and by the wavelength. From the second optical grating the light is directed to a detector 815. The second optical grating 813 is oriented so that only light having the desired wavelength travels to the detector, light of other wavelengths being refracted at other angles.

Figure 9:
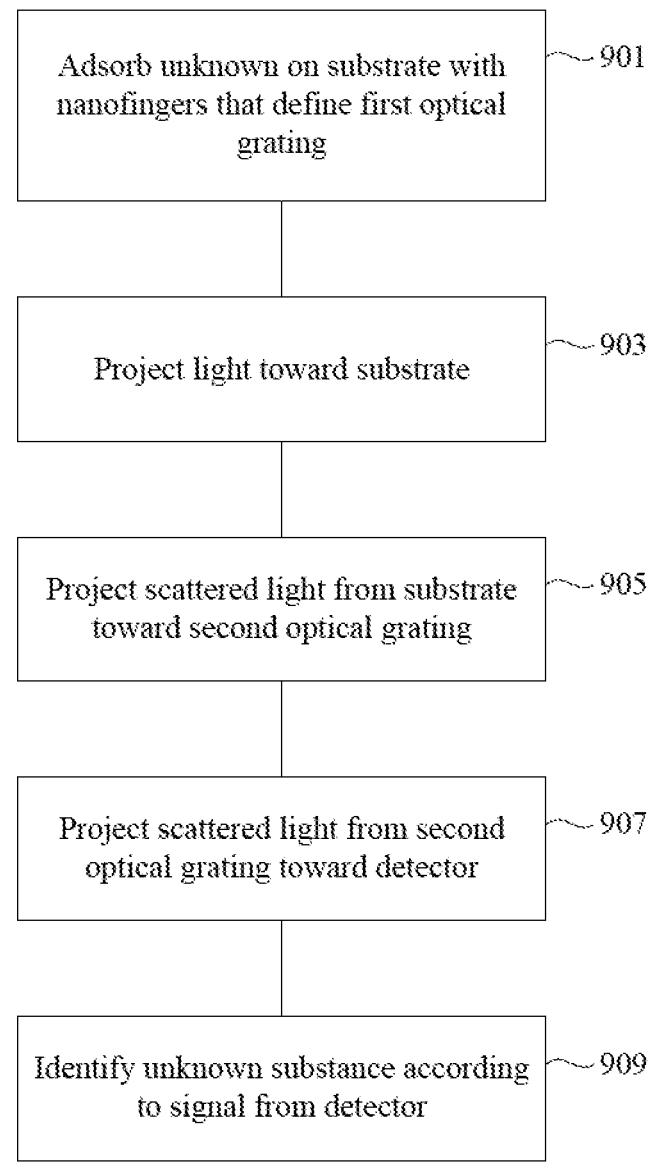
FIG. 9 is a flowchart illustrating an example of a method of analyzing an unknown substance using double-grating surface-enhanced Raman spectroscopy.

FIG. 9 illustrates an example of a method of analyzing an unknown substance using double-grating surface-enhanced Raman spectroscopy. The method includes adsorbing 901 an unknown substance on a substrate carrying nanofingers that define a first optical grating, projecting 903 a beam of light toward the substrate, projecting 905 light scattered from the substrate toward a second optical grating, projecting 907 light scattered from the second optical grating onto a detector, and identifying 909 the unknown substance according to a signal from the detector.

Identifying the unknown substance is done by conventional techniques, for example by comparing a spectrum as output by the detector with known spectra to find a match.

In some examples the second optical grating comprises a reflecting optical grating, and the method includes orienting the second grating to reflect the light toward the detector. In other examples the second optical grating comprises a transmissive optical grating, and the method includes orienting the second grating to refract the light toward the detector.

Arranging nanofingers on a SERS substrate to define a first optical grating and pairing the first optical grating with a complementary second optical grating provides a sensitive, low-cost, compact spectroscope that can meet the increasing demand for such an instrument.

We claim:

1. A double-grating surface-enhanced Raman spectrometer comprising:
   a substrate;
   a plurality of nanofingers carried by the substrate, the nanofingers arranged to define a first optical grating;
   a light source oriented to project a beam of light toward the first optical grating;
   a second optical grating oriented to receive a beam of light scattered from the first optical grating; and
   a detector oriented to receive a beam of light scattered from the second optical grating;
   wherein the nanofingers are to support an unknown substance;
   wherein the nanofingers are disposed relative to the light source and to the second optical grating such that only light having a wavelength of interest reflected from the first optical grating is incident on the second optical grating;
   and wherein the second optical grating is oriented with respect to a path of the wavelength of interest and the detector such that only light having the wavelength of interest is directed to the detector.

2. The spectrometer of claim 1 wherein the nanofingers are arranged in groups of four, and the groups define the first optical grating.

3. The spectrometer of claim 1 wherein the nanofingers are arranged in groups of four, the groups are arranged in rows, and the rows of groups define the first optical grating.

4. The spectrometer of claim 1 wherein the nanofingers are arranged in groups of four, the groups are arranged in rows and columns, and diagonals along groups in successive rows and columns define the first optical grating.

5. The spectrometer of claim 1 wherein the nanofingers are arranged in groups of three, and the groups define the first optical grating.

6. The spectrometer of claim 1 wherein the nanofingers are arranged in groups of five, and the groups define the first optical grating.

7. The spectrometer of claim 1 wherein the nanofingers are arranged in groups of six, and the groups define the first optical grating.

8. The spectrometer of claim 1 wherein the nanofingers are arranged in groups of seven, and the groups define the first optical grating.

9. The spectrometer of claim 1 wherein the second optical grating is oriented to reflect the scattered beam of light toward the detector.

10. The spectrometer of claim 1 wherein the second optical grating is oriented to refract the scattered beam of light toward the detector.

11. The spectrometer of claim 1 and further comprising an optical lens disposed between the first optical grating and the detector.

12. A method of analyzing an unknown substance using double-grating surface-enhanced Raman spectroscopy, the method comprising:
   adsorbing an unknown substance on a substrate carrying nanofingers that define a first optical grating;
   projecting a beam of light toward the substrate;
   projecting light scattered from the substrate toward a second optical grating;
   projecting light scattered from the second optical grating onto a detector; and identifying the unknown substance according to a signal from the detector;

wherein the nanofingers are disposed relative to the beam of light and to the second optical grating such that only light having a wavelength of interest reflected from the first optical grating is incident on the second optical grating;

and wherein the second optical grating is oriented with respect to a path of the wavelength of interest and the detector such that only light having the wavelength of interest is directed to the detector.

13. The method of claim 12 wherein projecting light from the substrate toward the second optical grating comprises orienting the second grating to reflect the light toward the detector.

14. The method of claim 12 wherein projecting light from the substrate toward the second optical grating comprises orienting the second grating to refract the light toward the detector.

15. The method of claim 12 and further comprising disposing an optical lens between the substrate and the detector.

16. The spectrometer of claim 1 wherein the nanofingers are projections on a substrate.

17. The method of claim 12 wherein the nanofingers are projections on a substrate.

18. The spectrometer of claim 1 wherein the second optical grating is oriented to receive light over a range of wavelengths from the first optical grating such that the two optical gratings determine a desired range of wavelengths such that any light not having a wavelength within the desired range is attenuated or does not reach the detector.

19. The method of claim 12 wherein the second optical grating is oriented to receive light over a range of wavelengths from the first optical grating such that the two optical gratings determine a desired range of wavelengths such that any light not having a wavelength within the desired range is attenuated or does not reach the detector.

* * * * *